(12) United States Patent
Geyer et al.

(10) Patent No.: US 8,822,368 B2
(45) Date of Patent: Sep. 2, 2014

(54) HYDROGENATION OF AROMATICS AND OTHER UNSATURATED ORGANIC COMPOUNDS

(75) Inventors: Reinhard Geyer, Leuna (DE); Klaus Hoheisel, Leuna (DE); Patrick Vander Hoogerstraete, Gent (BE); Jürgen Hunold, Leuna (DE); Michael Keck, Leuna (DE); Dirk Lose, Leuna (DE); Rainer Schödel, Leuna (DE)

(73) Assignee: Shell Oil Company, Houston, TX (US)

( * ) Notice: Subject to any disclaimer, the term of this patent is extended or adjusted under 35 U.S.C. 154(b) by 46 days.

(21) Appl. No.: 13/319,215

(22) PCT Filed: May 7, 2010

(86) PCT No.: PCT/EP2010/056253
§ 371 (c)(1),
(2), (4) Date: Nov. 30, 2011

(87) PCT Pub. No.: WO2010/128137
PCT Pub. Date: Nov. 11, 2010

(65) Prior Publication Data
US 2012/0065442 A1    Mar. 15, 2012

(30) Foreign Application Priority Data

May 7, 2009  (EP) .................................... 09159671
May 7, 2009  (EP) .................................... 09159674

(51) Int. Cl.
| | | |
|---|---|---|
| *B01J 23/755* | (2006.01) | |
| *B01J 21/04* | (2006.01) | |
| *B01J 21/16* | (2006.01) | |
| *B01J 21/06* | (2006.01) | |
| *C07C 5/10* | (2006.01) | |
| *B01J 35/00* | (2006.01) | |
| *B01J 35/10* | (2006.01) | |
| *B01J 37/02* | (2006.01) | |
| *B01J 23/80* | (2006.01) | |
| *B01J 21/12* | (2006.01) | |
| *B01J 37/18* | (2006.01) | |
| *B01J 37/14* | (2006.01) | |

(52) U.S. Cl.
CPC ............ *B01J 23/755* (2013.01); *B01J 35/0053* (2013.01); *B01J 35/006* (2013.01); *B01J 35/008* (2013.01); *C07C 5/10* (2013.01); *B01J 35/1061* (2013.01); *B01J 37/0205* (2013.01); *B01J 35/1038* (2013.01); *B01J 35/108* (2013.01); *B01J 21/12* (2013.01); *B01J 37/18* (2013.01); *B01J 23/80* (2013.01); *B01J 37/14* (2013.01); *B01J 21/04* (2013.01)
USPC ............ 502/259; 502/329; 502/335; 502/337

(58) Field of Classification Search
USPC .......... 502/259, 329, 335, 337; 585/270, 274, 585/276
See application file for complete search history.

(56) References Cited

U.S. PATENT DOCUMENTS

| | | | | |
|---|---|---|---|---|
| 4,490,480 | A   * | 12/1984 | Lok et al. ...................... | 502/315 |
| 6,689,712 | B1 * | 2/2004 | Tanaka ......................... | 502/305 |
| 2002/0016519 | A1 | 2/2002 | Lok .............................. | 585/276 |
| 2005/0203320 | A1* | 9/2005 | Ryu .............................. | 585/261 |
| 2008/0119354 | A1* | 5/2008 | Ryu .............................. | 502/314 |

FOREIGN PATENT DOCUMENTS

| | | | | |
|---|---|---|---|---|
| DE | 1263711 | 3/1968 | ............... | B01J 11/24 |
| DE | 4310971 | 10/1994 | ............... | B01J 23/74 |
| EP | 0290100 | 11/1988 | ............... | B01J 23/74 |
| EP | 0398446 | 11/1990 | ............... | B01J 35/02 |
| EP | 1262234 | 12/2002 | ............... | B01J 35/10 |
| GB | 926235 | 5/1963 | | |
| WO | WO2006079850 | 8/2006 | ............... | B01J 35/10 |

OTHER PUBLICATIONS

Fujitani T. et al.; "The Effect of Starting Source on the Concentration Distribution of Nickel Supported on Alumina"; Bulletin of the Chemical Society of Japan, Tokyo JP, vol. 62 pp. 2753-2755; Jan. 1, 1989.
Zielinski, J.; "Morphology of Nickel/Alumina Catalysts"; Journal of Catalysis;76; pp. 157-163, 1982.
Masaharu K., et al.; "On the Penetration Rate and the Role of Acids in the Control of Impregnation Profiles"; Bulletin of the Chemical Society of Japan;. 57 , pp. 1169-1173; 1984.

* cited by examiner

*Primary Examiner* — Jun Li

(57) ABSTRACT

The present invention relates to supported Ni-catalysts optionally comprising Zn as a promoter, methods for the production of said catalysts and uses of said catalysts for the hydrogenation of a hydrocarbon feed.

14 Claims, No Drawings

HYDROGENATION OF AROMATICS AND OTHER UNSATURATED ORGANIC COMPOUNDS

The present application claims priority from PCT/EP2010/056253, filed 7 May 2010, which claims priority from European Application 09159671.8, filed 7, May 2009 and European Application 09159674.2 filed 7 May 2009.

The present invention relates to hydrogenation catalysts and their preparation, as well as an associated process for the hydrogenation of aromatics and other unsaturated organic compounds such as olefins and carbonyl compounds.

The catalytic hydrogenation of aromatics is well known. DE 4 310 971 discloses a Ni—$Al_2O_3$ catalyst comprising contents of Ni (Nickel) from 10 to 60 weight-% for the hydrogenation of aromatic hydrocarbons. The Ni crystallites have an average diameter of 15 to 50 nm. Furthermore, the catalyst employed is characterised in that 15 to 75% of the pore volume is allotted to pores having a diameter of >100 nm. The large Ni crystallites indicate that the hydrating metal is used inadequately.

EP 0 290 100 relates to formed Ni-theta-$Al_2O_3$ catalysts comprising 5 to 40 weight-% of Ni for hydrogenation of hydrocarbons which contain aromatics. The catalyst support employed includes virtually no pores smaller than 2.0 nm. The Ni dispersion of the catalysts employed is very high. The surface area of Ni ranges from 80 to 300 $m^2$/g Ni. When used with feeds having a slightly higher content of sulphur these catalysts age very quickly, leading to a deterioration of their performance.

EP 0 398 446 discloses a catalyst system for hydrogenation of aromatics in solvents and white oil having high resistance against sulphur compounds. On a support the catalysts separately contain a hydrogenating component and a metal oxide. As metals Cu, Ni, Pt, Pd, Rh, Ru, Co and mixtures thereof and as a metal oxide component the oxides of Ag, La, Sb, V, Ni, Bi, Cd, Pb, Sn, V, Ca, Sr, Ba, Co, Cu, W, Zn, Mo, Mn, Fe and mixtures thereof are exemplified. According to this disclosure the catalyst may consist of $Al_2O_3$, $SiO_2$, $Al_2O_3.SiO_2$, $TiO_2$, $ZrO_2$ and MgO.

According to EP 0 974 637 even higher resistance against sulphur is achieved by a combination of a supported catalyst comprising noble metal, a catalyst comprising metal oxide and a Ni—$SiO_2$ catalyst. Thus, a supported Pt/Pd-catalyst is for example positioned at the reactor head and a mixture of ZnO extrudates and Ni—$SiO_2$ extrudates is placed below.

EP 1 262 234 discloses catalysts for the hydrogenation of aromatics comprising 0.1 to 2.0 weight-% of a group VIII noble metal on $SiO_2$—MgO support having a MgO content of 25 to 50 weight-% which show a low tendency to crack.

Those prior art catalysts comprising noble metal have the disadvantage that they are expensive. On the other hand, prior art Ni—$Al_2O_3$ catalysts, which are cheaper, are typically less effective and suffer from very high sensitivity to sulphur and chlorine compounds.

It is an object of the invention to provide a catalyst and a process for the hydrogenation of aromatics and other unsaturated organic compounds which overcomes at least one drawback associated with the prior art. Specifically, a technical problem underlying the present invention is to provide a catalyst and a process for the hydrogenation of aromatics and other unsaturated organic compounds which is particularly effective.

The present invention provides nickel (Ni)-catalysts which are highly effective and active in the hydrogenation of aromatics and other unsaturated organic compounds. Advantageously, the catalysts of the invention are also particularly poison resistant.

On the one hand, the invention is based on the appreciation that dispersion of Ni in a Ni-catalyst in a "semi-eggshell distribution", as further defined herein, contributes greatly to effectiveness of the catalyst in hydrogenation.

The term "semi-eggshell distribution" as used herein refers to a concentration distribution whereby the concentration in an outer shell region of the catalyst is higher than in a remaining centre of the catalyst, in particular as detailed below.

Thus, according to a first aspect, the invention resides broadly in a Ni catalyst comprising a support and Ni wherein a centre of the catalyst comprises a base Ni concentration and a remaining outer shell region of the catalyst comprises an increased Ni concentration.

The invention is also based on the appreciation that a multimodal, specifically bimodal, particle size distribution of Ni crystallites, as further defined herein, contributes significantly to the effectiveness of Ni catalysts in hydrogenation.

Therefore, according to a second aspect, the invention resides broadly in a Ni catalyst comprising a support and Ni, wherein the size distribution of Ni crystallites of the catalyst is bimodal, with a first proportion of the Ni crystallites having an average size (diameter) of 1.0 to 2.5 nm and a second, remaining proportion of the Ni crystallites having an average size (diameter) of 3.0 to 4.5 nm.

A particular synergy has been observed by the inventors in Ni catalysts between semi-eggshell Ni distributions and bimodal Ni crystallite size distributions, as defined herein. In particular, without wishing to be bound by theory, it is thought that in those catalysts of the invention which exhibit both a semi-eggshell distribution of Ni and a bimodal Ni crystallite size distribution, larger Ni crystallites are particularly prominent in the outer shell region of the catalyst (i.e. more prominent than in the centre), thereby helping to shield smaller and more active Ni crystallites in the centre of the catalyst from catalyst poisons.

Thus, according to a third aspect, the invention resides broadly in a Ni catalyst comprising a support and Ni, wherein Ni is dispersed in a semi-eggshell distribution as defined anywhere herein, and wherein the size distribution of the Ni crystallites of the catalyst is bimodal as defined anywhere herein.

For example, the invention provides a particularly effective solution to the underlying technical problem by residing, according to a fourth aspect, in a Ni-catalyst, comprising a support and Ni, wherein the size distribution of the Ni crystallites is bimodal with 30 to 70% of the Ni crystallites having an average size of 1.0 to 2.5 nm and the remaining Ni crystallites having an average size of 3.0 to 4.5 nm, and wherein the Ni is distributed in an outer shell region of the catalyst having a penetration depth of 3 to 15% of the catalyst diameter and the centre of the catalyst in a concentration ratio in the range of from 3.0:1 to 1.3:1 (outer shell:centre) which hereinafter is abbreviated as 3.0 to 1.3.

In the context of the present invention, the diameter of a catalyst (i.e. catalyst particle) is the longest internal straight length of said catalyst passing through the geometric middle of the catalyst. The geometric middle lies in the catalyst centre and is the point, or plurality of points, having the greatest minimum distance from the catalyst surface. The geometric middle may correspond to the centre of gravity of the catalyst, provided that it falls within the catalyst.

The term "penetration depth" is used herein as a parameter for defining the thickness of the outer shell region, and consequently also the dimensions of the catalyst centre, which makes up the remainder of the catalyst. The penetration depth defines the cross-sectional depth of the outer shell region and therefore equals the distance between the surface of the catalyst and the circumference of the catalyst centre.

The penetration depth may be an assigned depth value, taken for example to be a defined percentage of the catalyst diameter, or an absolute distance. The assigned depth value may be set as any number falling within any of the penetration depth ranges (relative or absolute) disclosed herein. Alternatively, the penetration depth may be defined by a range of assigned depth values.

The penetration depth may correspond to an actual penetration depth value. The actual penetration depth value of the catalyst is defined as the minimum cross-sectional depth (measured from the catalyst surface in increments of 5 μm in the direction of the nearest point of the geometric middle of the catalyst) at which the Ni concentration lies within plus or minus (±) 10% of the Ni concentration at the geometric middle of the catalyst. Where the geometric middle comprises a plurality of points, the Ni concentration at the geometric middle is taken as an average (measured at 5 μm intervals if the points are continuous). The Ni concentration at the geometric middle is determined in weight-% and rounded up to the nearest weight-%.

Thus, aspects of the present invention envisage a very specific Ni-distribution provided over substantially the entire cross-section of a catalyst (or catalyst particle) in a semi-eggshell distribution such that the Ni is distributed in an outer shell region and the centre of the catalyst in a range of concentration ratios of from 3:1 to 1.3:1, which equals a range of concentrations from 3.0 to 1.3, each ratio calculated as Ni concentration in the outer shell region of the catalyst having a penetration depth of 3 to 15% of the catalyst diameter to the Ni concentration in the centre of the catalyst.

Surprisingly, it has been found that the catalysts of the present invention, which typically do not exhibit the large surface areas disclosed in EP 0 290 100, still have high performance. This is particularly noted where the invention foresees a semi-eggshell distribution of the Ni in the catalyst in combination with a particular size distribution of Ni crystallites. Furthermore, the catalysts of the present invention have the advantage that production costs are low. The catalysts of the present invention also provide advantageous resistance against contamination with sulphur and chlorine compounds.

Advantageously, the ratio of the Ni concentration in the outer shell region to the Ni concentration in the centre of the catalysts according to the invention may be in a range from 3.0:1 to 1.3:1, preferably 3.0:1 to 1.5:1, more preferably 2.8:1 to 1.4:1 or 2.5:1 to 1.5:1, and in particular 2.5:1 to 1.3:1 (each outer shell:centre).

The Ni concentration in the outer shell region and the centre of the catalyst is determined in weight-%.

The Ni concentration in the outer shell region is conveniently determined by measuring at 5 μm intervals, from the surface of the catalyst towards the nearest point of the geometric middle of the catalyst, and taking an average of the resultant Ni concentration readings. The concentration in the outer shell region is rounded to the nearest weight-%.

The Ni concentration in the centre of the catalysts of the invention may typically be homogenous or substantially homogenous (i.e. vary by less than ±10%). Where variations in Ni concentration occur, an average of measurements at 5 μm intervals is taken as the concentration in the centre. The concentration in the catalyst centre is rounded to the nearest weight-%.

The outer shell region of the catalysts according to the invention may advantageously be characterized by a maximum penetration depth of up to 15%, 13%, 10%, 8% or 7% of the catalyst diameter. A minimum penetration depth may be 3%, 5%, or 7% of the catalyst diameter. Specifically, the penetration depth may lie in the range of from 3 to 15% of the catalyst diameter, preferably in the range of from 3 to 10%, more preferably in the range of from 3 to 8%, and in particular in the range of from 3 to 7%, of the catalyst diameter.

A single cross-section may be taken as representative in defining the catalysts of the invention. Thus, the invention encompasses any catalyst having at least one cross section that conforms to the definitions (e.g. relating to penetration depth, outer shell and centre) provided herein. Preferably all cross sections of the catalysts may fall within the definitions provided herein.

Advantageously, the average size (diameter) of the Ni crystallites of the catalysts of the invention may be from 1.0 to 4.0 nm, preferably from 1.5 to 3.5 nm, more preferably 1.6 to 2.4. In preferred embodiments of the present invention, the size (diameter) distribution of the Ni crystallites may be bimodal. In particularly preferred embodiments, the present invention foresees a bimodal size distribution, wherein 30 to 70%, preferably 40 to 60%, more preferably 45 to 55% of the particles have an average size of 1.0 to 2.5, preferably 1.2 to 2.2, more preferably 1.4 to 2.0, in particular 1.6 nm and the remaining percentage of the particles adding up to 100% have a different average size, in particular 70 to 30% of the particles, preferably 60 to 40%, more preferably 55 to 45% of the particles have an average size of 3.0 to 4.5, preferably 3.2 to 4.2, more preferably 3.4 to 4.0.

In further preferred embodiments of the present invention, the pore volume of the catalysts may be 0.2 to 0.7 ml/g, preferably 0.3 to 0.6 ml/g, more preferably 0.4 to 0.5 ml/g.

Advantageously, the portion of the pore volume having pore radii of >5.0 nm may be 75 to 100%, preferably 75 to 90%, more preferably 75 to 80%, in particular at least 75.5%, preferably 75.5 to 100% or 75.5 to 90%.

In further preferred embodiments of the present invention, the Ni content in the catalysts may be 5 to 70 weight-%, preferably 10 to 60 weight-%, and most preferably 10 to 35 weight-%. A minimum Ni content of 18 weight-% is also preferred.

Preferably, the Ni content in the catalysts may be 10 to 24 weight-%. In particular, the Ni content in the catalysts may be 10 to 24 weight-% and the concentration ratio of Ni of the outer shell region of the catalysts to the Ni of the centre of the catalysts may be in a range from 2.5 (2.5:1) to 1.3 (1.3:1).

Alternatively, the Ni content in the catalysts may advantageously be 24.1 to 35 weight-%. In particular, the Ni content in the catalyst may be 24.1 to 35 weight-% and the concentration ratio of the Ni of the outer shell region to the Ni of the centre of the catalyst may be in a range from 3.0 (3.0:1) to 1.5 (1.5:1).

The term "weight-%" as used herein refers, if not otherwise stated, to the percentage weight relative to the weight of the dry catalyst, and "weight-%" values are based on elemental form unless specified otherwise. In the context of the present invention, the components of the catalysts are to be selected in an overall amount to add up to 100 weight-%, most preferably not to exceed 100 weight-%.

In further preferred embodiments of the present invention, the specific Ni surface area of the catalysts may be ≤150 m²/g Ni, in particular 10 to 140 m²/g Ni, preferably ≤135 m²/g Ni, preferably 80 to 135 m²/g Ni.

In preferred embodiments of the present invention, the support of the catalyst may comprise, preferably essentially consist of, particularly consist of, $Al_2O_3$, $Al_2O_3.SiO_2$ or a mixture of $Al_2O_3$ and $Al_2O_3.SiO_2$. The $Al_2O_3$ may preferably comprise gamma and/or theta alumina.

In further preferred embodiments of the present invention, the support of the catalyst may comprise $Al_2O_3$ having surface areas (BET surface areas) of 100 to 220 $m^2/g$, preferably of 120 to 220 $m^2/g$, more preferably of 140 to 220 $m^2/g$, in particular preferably of 160 to 220 $m^2/g$. In further preferred embodiments of the present invention, the support may comprise $Al_2O_3.SiO_2$ having surface areas of 120 to 200 $m^2/g$, preferably of 140 to 200 $m^2/g$, more preferably of 160 to 200 $m^2/g$.

In further preferred embodiments of the present invention, the $SiO_2$ content of the support, in particular the $Al_2O_3.SiO_2$ support, may be 2 to 8 weight-%, preferably 2 to 4 weight-%, the support adding up to 100 weight-% with $Al_2O_3$.

The Ni catalysts of the present invention contain Ni in either its elemental or combined form, preferably in its elemental form.

Advantageously, the catalysts of the present invention may be free of noble metals. In preferred embodiments the catalysts of the present invention are free of metals from the group I, VIII or both of the periodic table of the chemical elements. Preferably, Ni may be the only hydrogenation-active metal present in the catalyst.

In further preferred embodiments of the present invention, the catalysts or catalyst particles may be shaped, for example in the form symmetrical or asymmetrical extrudates, tablets, rings or spheres. Further suitable forms are cylindrical particles, which may be hollow or not, as well as polylobed particles, preferably with 2, 3 or 4 lobes. Preferably, the catalyst may have a diameter from 0.5 to 20 mm, preferably 1 to 15 mm, 1 to 10 mm, 1 to 5 mm, 1 to 3 mm.

As aforesaid, in the context of the present invention, a diameter of a catalyst or catalyst particle is the longest internal straight length of said catalyst or catalyst particle passing through the geometric middle of the catalyst.

The penetration depth of the catalysts may typically be in the range of from 40 to 195 µm, preferably 50 to 150 µm, even more preferably 60 to 110 µm, and most preferably 70 to 105 µm.

Preferably, the centre of the catalysts may have a diameter (e.g. spherical) of 200 to 600 µm, preferably of 300 to 500 µm, more preferably of 350 to 450 µm, in particular of 400 µm. In the context of the present invention, a diameter of the centre is the longest internal straight length of the centre passing through the geometric middle of the catalyst.

The centre of the catalysts may advantageously be defined as an interior region including and surrounding the geometrical middle of the catalysts, preferably with a radius (e.g. spherical) of +/−170 to 230 µm, in particular 200 µm around the geometrical middle. The centre of the catalyst may make up 50 to 90%, preferably 60 to 80% by weight of the catalyst or catalyst particle, with the outer shell region making up the rest.

The dimensions of the outer shell region and the centre of the catalyst may also be defined with reference to their overall Ni content. The outer shell region of the catalyst may advantageously comprise up to 30% of the overall Ni content of the catalyst. Thus the outer shell region may advantageously be defined as the outermost shell region of the catalyst (or catalyst particle) comprising 30%, preferably 20% and most preferably 15% of the Ni in the catalyst. Outermost refers to maximum distance from the geometrical middle of the catalyst.

The Ni-catalysts of the present invention may advantageously comprise an amount of promoting metal Zinc (Zn). Although the catalysts of the invention display good poison resistance even in the absence of Zn, the inventors have found that the presence of Zn advantageously makes the catalysts especially suitable for the hydrogenation of aromatics and other unsaturated organic compounds where the feed contains a sulphur component, a chlorine component or both, for instance in the range of 0.5 to 2 ppm.

Accordingly, the catalysts of the invention may advantageously comprise Zn in an amount of 1 to 5% by weight (weight-%), preferably 2 to 4% by weight, and in particular 2 to 3.5% by weight.

The Zn may be dispersed in a semi-eggshell distribution as defined anywhere herein, or may be distributed substantially homogeneously in the catalyst. Zn may be present in elemental form and/or in combined form.

A further subject of the present invention is a process for the preparation of the, preferably shaped, and supported Ni-catalysts of the present invention.

Thus, according to a fifth aspect, the present invention resides in a process or method for the preparation of a Ni-catalyst according to the present invention, wherein Ni or a compound containing Ni is contacted with a support so as to obtain said catalyst.

According to a sixth aspect, the present invention resides broadly in a process or method of making a nickel (Ni)-catalyst the method comprising subjecting a support to at least two impregnations, preferably by spraying, with a Ni solution, each impregnation being followed by a drying step to release a Ni precursor from the solution and a calcination step to convert the Ni precursor to Ni crystallites. This method provides particularly advantageous catalysts in accordance with the invention.

Specifically, without wishing to be bound by theory, it is thought that impregnation by spraying, particularly in combination with relatively mild drying, calcination and other process features as defined herein, enables the production of advantageous catalysts with a semi-eggshell distribution of Ni and a bimodal particle size distribution of Ni crystallites.

In a preferred embodiment of the present invention, the process for the preparation of the Ni-catalyst comprises spraying an ammoniacal solution of a Ni salt onto an $Al_2O_3$ and/or $Al_2O_3.SiO_2$ support, for example as defined above.

In a further preferred embodiment of the present invention, the volume of the ammoniacal solution used in impregnation may be 100 to 115%, preferably 110 to 115%, of the pore volume of the support. Furthermore, advantageously, the volume of the solution may be 100 to 115%, preferably 110 to 115%, of the pore volume of the impregnated, dried and calcined intermediate.

In a further preferred embodiment of the present invention, the process for the preparation of the Ni catalyst may include at least three impregnation steps. Preferably, three impregnation steps are foreseen to adjust a preferred Ni content of the catalyst of >24 weight-%.

In a preferred embodiment of the present invention, the ammoniacal solution of Ni salt may be produced by dissolving $Ni(OH)_2$ and/or $NiCO_3$ in ammonia and/or ammonium carbonate and/or ammonium hydrogen carbonate.

In a preferred embodiment of the present invention, the Ni concentration of the solution of Ni salt may be from 100 to 200 g Ni/l, 110 to 190 g Ni/l, in particular of 120 to 180 g Ni/l.

In a further preferred embodiment of the present invention, a drying step may be carried out after each step of impregnation. Preferably, the drying step may be carried out at temperatures of 80 to 200° C., preferably of 90 to 140° C., in particular of 100 to 130° C. The drying time may preferably be at least 30 minutes, preferably at least 1 hour, more preferably at least 3 hours. The drying time may advantageously be at most 24 hours, preferably at most 12 hours, most preferably at most 6 hours.

In a further preferred embodiment of the present invention, an (intermediate) annealing or calcination step may be carried out after the drying step. Preferably, the annealing step may be carried out at temperatures of 200 to 400° C., preferably of 220 to 380° C., in particular of 250 to 350° C. The annealing time may preferably be at least 30 minutes, preferably at least 1 hour, more preferably at least 3 hours. The annealing time may advantageously be at most 12 hours, preferably at most 8 hours, most preferably at most 6 hours.

As the catalysts of the invention may advantageously comprise an amount of promoting metal such as Zn, the methods or processes of making catalysts of the invention may comprise contacting an amount of Zn with the support. Specifically, the preferably ammoniacal impregnation solution of Ni salt may comprise at least one Zn salt (e.g. zinc carbonate). Zn may advantageously be present in any of the Ni impregnation solutions described herein at a concentration of 5 to 25 g Zn/l, preferably 10 to 20 g Zn/l and in particular 17 to 20 g Zn/l.

In a furthermore preferred embodiment of the present invention, the catalysts prepared according to the invention may be subjected to a treatment with hydrogen or hydrogen-comprising gas thereby resulting in a reduction step. In preferred embodiments the catalysts are further stabilised in an oxygen-containing nitrogen stream.

In preferred embodiments of the invention, the reduction degree in the reduced and stabilised catalysts may be 50 to 95%, preferably 60 to 90% and in particular 75 to 85%. The reduction degree is defined as the percentage ratio of Ni metal by weight to overall Ni content by weight.

The present invention also encompasses the use of the catalysts described herein in the hydrogenation of a hydrocarbon feed. According to a seventh aspect, the invention resides in a process for the hydrogenation of a hydrocarbon feed, wherein the hydrocarbon feed is hydrogenated under suitable hydrogenation conditions in the presence of a Ni-catalyst according to the present invention and hydrogenated hydrocarbons are obtained.

In a preferred embodiment of the present invention, the hydrocarbon feed may be a feed containing unsaturated aromatic or unsaturated non-aromatic hydrocarbons. Preferably, the unsaturated organic compounds may be olefins or carbonyl compounds. To make use of the improved poison resistance of the catalysts of the invention, the hydrocarbon feed may preferably comprise a sulphur component, a chlorine component or both, for instance in the range of 0.5 to 2 ppm. The processing of such feeds may be accomplished particularly effectively when the Ni-catalyst according to the invention comprises an amount of Zn, as specified above.

In a further preferred embodiment of the present invention, the process for the hydrogenation is carried out at a reaction pressure of 1 to 100 bar, preferably of 1 to 50 bar, preferably of 10 to 40 bar.

In a further preferred embodiment of the present invention, the process for the hydrogenation is carried out at a reaction temperature of 50 to 250° C., of 80 to 220° C., preferably of 60 to 90° C.

In a preferred embodiment of the present invention, the process for the hydrogenation is carried out at a LHSV (liquid hourly space velocity) of 0.2 to 7, preferably 1 to 7, preferably of 2 to 6 v/vh (volume gas per volume of catalyst and hour).

In a further preferred embodiment of the present invention, the process for the hydrogenation is carried out at a ratio of gas to product of 100 to 700:1, preferably 200 to 600:1 of the hydrocarbon feed.

Further preferred embodiments are the subject-matter of the sub-claims.

Unless indicated otherwise, parameters recited herein are based on standard measuring techniques (ISO, if available). Notably, the following specific techniques are employed in the context of the invention, supplemented as necessary by standard techniques and variables.

The Ni content (Weight-% Ni) in the catalysts is determined by complexometric titration with murexide as indicator. Before the measurements the catalyst samples are dissolved in sulphuric acid (25%) by using a microwave treatment.

The Ni metal content of the catalysts is determined by using a volumetric method. After pre-treatment of the reduced and stabilized catalyst samples for 1 h at 250° C. in a hydrogen stream the catalysts are treated with hydrochloric acid and the generated hydrogen is measured. The nickel metal content is calculated by using the following formula: Nickel metal content (%)=273×2.62×a×b/10×760×(273*T)×E wherein: a=air pressure (Torr); b=measured gas volume (ml); T=temperature (° C.); E=catalyst weight (g).

The Zn content (Weight-% Zn) the catalysts is determined by X-ray fluorescence analysis, specifically analysis method S4 Explorer from Bruker AXS.

The metal concentration in particular parts of the catalysts or catalyst particles (i.e. concentration distribution) is determined by WDX-EPMA using scanning electron microprobe quantometer (SEMQ, ARL, USA), Analyzing crystals: LiF for Nickel and Zinc, Multilayer for Oxygen and RAP for Alumina, Accelerating potential 25 kV, sample current 30 nA, up to 25 measure points in interval of 5 μm. Before the measurements the catalyst samples were carbon coated.

Ni crystallite size and crystallite size distribution are determined by X-ray diffraction, based on the Scherrer relationship. The processing of the data was carried out with RAYFLEX software from SEIFERT FPM. The ICDD database (PDF-2 Release 2004) was used for the identification of the phase structures. The X-ray diffractometer used was an XRD7 from Rich. Seifert & CO. The scattering curve sections were recorded perpendicularly to the (220) lattice plane from the interference line spreading under the following conditions:

| | |
|---|---|
| Generator data | 34 kV/30 mA |
| Goniometer | XDR7 |
| Radiation | Cu-Kα |
| Filter | Ni |
| Angular range | 2 theta = 70.0-83.0° |
| Step width | Δ = 0.05° |
| Count time | 10 sec |

Conclusions on the modality (mono Gauss-line profile or bimodal Gauss-line profile) of the Ni-(220) line profile were obtained by use of the peak fit program PF4 from Jandel Corporation. Before the XRD measurements all catalyst samples were reduced for 1 h at 250° C. in a hydrogen stream and then embedded in oil.

The BET surface area of the supports and catalysts is determined by using the $N_2$ adsorptions technique according to Analytical Methods in Fine Particle Technology, Micromeritics 1997, p. 60, P. A. Webb and C. Orr, 5 points evaluation at p/p0 from 0.05 . . . 0.20. Before the measurements all samples were treated for 30 minutes at 200° C. in a nitrogen stream.

Ni surface areas are determined by hydrogen chemisorption after a reduction of 250° C. according to the volumetric process by means of ASAP 2010 of Micromeritics (Analytical Methods in Fine Particle Technology, Micomeritics 1997, p. 227, P. A. Webb and C. Orr). Before measuring the Ni surface area at 30° C. the fresh reduced catalyst samples were treated in vacuum at 450° C. to remove of any water in the samples.

Pore volume was calculated from the envelope density by using Mercury and absolute density values by using Helium for the same sample (according to Analytical Methods in Fine Particle Technology, Micromeritics 1997, p. 11, P. A. Webb and C. Orr).

Pore size distribution is determined according to Analytical Methods in Fine Particle Technology, Micromeritics 1997, chapter 4: Pore Structure by Mercury Intrusion Porosimetry, p. 155, P. A. Webb and C. Orr with Autopore IV 9500 from Micromeritics (Contact Angle: 141.3 degrees, Hg surface Tension: 480.5 dynes/cm). Before the pore volume and distribution measurements all samples were pre-treated for 2 hours at 100° C. in air.

The advantages of the present invention shall be further illustrated by way of the following examples and comparisons.

Five catalysts according to the invention were prepared in Examples 2 to 6 for comparison with prior art catalysts prepared in Examples 1 and 7.

EXAMPLE 1

Comparative 200 g of a typical theta alumina support in form of 1.3 mm Trilobes with a BET surface area of 110 m$^2$/g and a total pore volume of 0.79 cm$^3$/g are impregnated with a nickel amine carbonate complex solution. The nickel content in the solution was 120 g Nickel/l solution. The impregnation was carried out by submersion of the support into the Ni containing solution (approximately twice the total pore volume was used). After ten minutes the excess of the solution was separated, the impregnated extrudates were dried at temperatures of about 120° C. for 12 h and calcined at 350° C. for 4 h. In order to get a nickel content in the ready catalyst of about 28 weight-% it was necessary to carry out four impregnation, drying and calcination steps. The calcined catalyst precursor was reduced in a hydrogen stream at a temperature of 450° C. and stabilized in a nitrogen flow containing 0.1 vol.-% oxygen at temperatures up to 80° C., increasing the oxygen concentration slowly to 2.5 vol.-%.

The characteristics of the resultant reduced and stabilised catalyst were as follows:

| Example 1 | |
|---|---|
| Nickel content | 28.9 weight-% |
| Nickel metal content | 22.3 weight-% |
| Nickel-surface area | 149 m$^2$/g Nickel |
| Penetration depth defining outer shell region having increased Ni-concentration (single cross-section measurement) | 100 μm |
| Ratio of concentration of Ni outer shell region:Ni of centre app. | 1.2 |
| Nickel crystallite average size (diameter) | 2.5 nm |
| Modality of Ni crystallite size (diameter) distribution | Monomodal |
| Pore volume | 0.42 cm$^3$/g |
| Portion of pores having pore radii >5 nm | 53.3% |

EXAMPLE 2

According to the Invention 200 g of a alumina silica (2.5% SiO$_2$) support in form of 1.3 mm Trilobes with a BET surface area of 162 m$^2$/g and a total pore volume of 0.88 cm$^3$/g are impregnated by spraying with 195 ml of a nickel amine carbonate complex solution (about 110% of the pore volume of the support), which is obtained by dissolving nickel hydroxycarbonate in a mixture of ammonia and ammonium carbonate. The nickel content in the solution was about 180 g Nickel/l solution. After the impregnation the intermediate was dried at 120° C. for 12 h and calcined at 330° C. for 4 h. A second and third impregnation of the dried and calcined intermediate was carried out by using the same nickel containing solution (about 110% of the pore volume of the dried, calcined support). Subsequently, the catalyst precursor was reduced in a hydrogen stream at temperatures of 400° C. and stabilized by using an oxygen containing gas stream (oxygen content 0.1 vol.-% up to 2 vol.-%).

The characteristics of the resultant reduced and stabilised catalyst were as follows:

| Example 2 | |
|---|---|
| Nickel content | 28.3 weight-% |
| Nickel metal content | 24.9 weight-% |
| Nickel-surface area | 134 m$^2$/g Nickel |
| Penetration depth defining outer shell region having increased Ni-concentration (single cross-section measurement) | 100 μm |
| Ratio of concentration of Ni outer shell region:Ni of centre app. | 1.8 |
| Nickel crystallite average size (diameter) | 2.7 nm |
| Modality of Ni crystallite size (diameter) distribution | Bimodal 48% of the crystallites have an average size of 1.6 nm 52% of the crystallites have an average size of 3.7 nm |
| Pore volume | 0.42 cm$^3$/g |
| Portion of pores having pore radii >5 nm | 75.8% |

EXAMPLE 3

According to the Invention 200 g of a gamma and theta alumina support in form of 1.3 mm Trilobes with a BET surface area of 143 m$^2$/g and a total pore volume of 0.87 cm$^3$/g are impregnated by spraying with 200 ml of a nickel amine carbonate complex solution (about 115% of the pore volume of the support), which is obtained by dissolving nickel hydroxy carbonate in a mixture of ammonia and ammonium carbonate. The nickel content in the solution was about 175 g Nickel/l solution. After the impregnation the intermediate was dried at 120° C. for 12 h and calcined at 330° C. for 4 h. A second and third impregnation of the dried and calcined intermediate was carried out by using the same nickel containing solution (about 115% of the pore volume of the dried, calcined support). Subsequently, the catalyst precursor was reduced in a hydrogen stream at temperatures of 400° C. and stabilized by using an oxygen containing gas stream (oxygen content 0.1 vol.-% up to 2 vol. %).

The characteristics of the resultant reduced and stabilised catalyst were as follows:

| Example 3 | |
|---|---|
| Nickel content | 28.6 weight-% |
| Nickel metal content | 24.6 weight-% |
| Nickel-surface area | 128 m²/g Nickel |
| Penetration depth defining outer shell region having increased Ni-concentration (single cross-section measurement) | 75 µm |
| Ratio of concentration of Ni outer shell region:Ni of centre app. | 2.1 |
| Nickel crystallite average size (diameter) | 2.8 nm |
| Modality of Ni crystallite size (diameter) distribution | Bimodal 55% of the crystallites have an average size of 1.5 nm 45% of the crystallites have an average size of 4.3 nm |
| Pore volume | 0.44 cm³/g |
| Portion of pores having pore radii >5 nm | 83.7% |

EXAMPLE 4

According to the Invention 200 g of the described support from example 3 are impregnated by spraying with 200 ml of a nickel amine carbonate complex solution (115% of the pore volume of the support), which is obtained by dissolving nickel hydroxy carbonate in a mixture of ammonia and ammonium carbonate. The nickel content in the solution was about 183 g Nickel/l solution. After the impregnation the intermediate was dried at 120° C. for 12 h and calcined at 330° C. for 4 h. A second impregnation of the dried and calcined intermediate was carried out by using the same nickel containing solution (115% of the pore volume of the dried, calcined support). Subsequently, the catalyst precursor was reduced in a hydrogen stream at temperatures of 400° C. and stabilized by using a oxygen containing gas stream (oxygen content 0.1 vol.-% up to 2 vol.-%).

The characteristics of the resultant reduced and stabilised catalyst were as follows:

| Example 4 | |
|---|---|
| Nickel content | 23.6 weight-% |
| Nickel metal content | 18.6 weight-% |
| Nickel-surface area | 130 m²/g Nickel |
| Penetration depth defining outer shell region having increased Ni-concentration (single cross-section measurement) | 70 µm |
| Ratio of concentration of Ni outer shell region:Ni of centre app. | 1.6 |
| Nickel crystallite average size (diameter) | 2.3 nm |
| Modality of Ni crystallite size (diameter) distribution | Bimodal 60% of the crystallites have an average size of 1.3 nm 40% of the crystallites have an average size of 3.1 nm |
| Pore volume | 0.48 cm³/g |
| Portion of pores having pore radii >5 nm | 87.0% |

EXAMPLE 5

According to the Invention 200 g of a gamma and theta alumina support in form of 1.3 mm Trilobes with a BET surface area of 143 m²/g and a total pore volume of 0.85 cm³/g are impregnated by spraying with 190 ml of a nickel and zinc containing complex solution (about 112% of the pore volume of the support), which is obtained by dissolving nickel hydroxy carbonate and zinc carbonate in a mixture of ammonia and ammonium carbonate. The solution contains about 175 g Nickel/l solution and 12 g Zn/l solution. After the impregnation the intermediate was dried at 120° C. for 12 h and calcined at 350° C. A second and third impregnation of the dried and calcined intermediate was carried out by using the same nickel and zinc containing solution (about 112% of the pore volume of the dried, calcined support). Subsequently, the catalyst precursor was reduced in a hydrogen stream at temperatures of 400° C. and stabilized by using an oxygen containing gas stream (oxygen content 0.1 vol. % up to 2 vol. %).

The characteristics of the resultant reduced and stabilised catalyst were as follows:

| Example 5 | |
|---|---|
| Nickel content | 29.1 weight-% |
| Zinc content | 2.0 weight-% |
| Nickel metal content | 23.2 weight-% |
| Nickel-surface area | 110 m²/g Nickel |
| Penetration depth defining outer shell region having increased Ni-concentration (single cross-section measurement) | 110 µm |
| Ratio of concentration of Ni outer shell region:Ni of centre app. | 1.9 |
| Nickel crystallite average size (diameter) | 2.7 nm |
| Modality of Ni crystallite size distribution | Bimodal 45% of the crystallites have an average size of 1.8 nm 65% of the crystallites have an average size of 3.5 nm |
| Pore volume | 0.45 cm³/g |
| Portion of pores having pore radii >5 nm | 80.3% |

EXAMPLE 6

According to the Invention 200 g of the alumina support described in example 5 are impregnated by spraying with 187 ml of an ammoniacal Ni/Zn complex solution, which contains 170 g Ni/l and 18 g Zn/l solution, are dried and calcined. Using this intermediate two further impregnations are carried out. In all three impregnation steps the volume of the solution was about 110% of the pore volume of the used support or the dried and calcined intermediate. After the reduction of the material at 420° C. in a hydrogen stream and the subsequent described stabilization using an oxygen containing gas stream (oxygen content 0.1 vol. % up to 2 vol. %).

The characteristics of the resultant reduced and stabilised catalyst were as follows:

| Example 6 | |
|---|---|
| Nickel content | 28.5 weight-% |
| Zinc content | 3.1 weight-% |
| Nickel metal content | 24.2 weight-% |
| Nickel-surface area | 100 m$^2$/g Nickel |
| Penetration depth defining outer shell region having increased Ni-concentration (single cross-section measurement) | 115 μm |
| Ratio of concentration of Ni outer shell region:Ni of centre app. | 2.2 |
| Nickel crystallite average size (diameter) | 2.9 nm |
| Modality of Ni crystallite size distribution | Bimodal 40% of the crystallites have an average size of 1.9 nm 60% of the crystallites have an average size of 3.8 nm |
| Pore volume | 0.44 cm$^3$/g |
| Portion of pores having pore radii >5 nm | 78.7% |

COMPARATIVE EXAMPLE 7

According to EP 0 398 446

A prior art catalyst was produced according to the impregnating process of EP 0 398 446.

200 g of aerosil 200 powder (manufactured by DEGUSSA) was suspended in 10 l condensate water. To this suspension were added Ni chloride and urea. After adding the slurry temperature was raised up to 90° C. under stirring. After about 8 h the precipitation suspension was cooled down, filtered and washed with 15 l condensate water. The obtained filter cake was re-dispersed into 5 l condensate water and under stirring an Iron (III) chloride solution was added. During the injection the pH value was maintained at 5.5 by additional injection of an alkaline solution. Then the suspension was filtered and the washed with condensate water. After drying at about 110° C. the precursor material was grinded and then formed to 1.4 mm cylindric extrudates by using water and methylcellulose as binder. The extrudates were reduced in a hydrogen stream at 450° C. for 6 h and stabilized by using a nitrogen-oxygen mixture.

The reduced and stabilized catalyst contains 13.5 wt.-% Nickel and 9.4 wt.-% Iron. The metal reduction degree was about 85%, the Nickel-metal surface area is about 60 m2/g Ni.

Comparison 1

The higher performance of the catalysts of the present invention is illustrated by a comparison of the hydrogenation performance of the prior art catalyst of Example 1 with the that of the catalysts of Examples 2 to 4.

The hydrogenation of a mixture of o-xylol and cyclohexane was carried out under identical conditions, using catalysts according to Examples 1 to 4. The hydrogenation was carried out in an integral flow reactor (internal diameter: 25 mm). The integrated catalyst volume was 25 ml. Said 25 ml of catalyst were each introduced in 20 portions with 20 portions of SiC in a volume ratio of 1:1. Prior to catalytic reaction the catalysts were reactivated in a stream of hydrogen (50 l/h) at 250° C. over a period of 4 h. As a feed a mixture, o-xylol-cyclohexane having a content of aromatics of 25 weight-% and a content of sulphur of 1.1 ppm in the form of benzothiophene was employed. Further process conditions are the following: reaction pressure 30 bar, reaction temperature 70° C., reaction time 40 h, LHSV 4 V/V h, ratio of gas/product 400 l H$_2$/l mixture of o-xylol-cyclohexane.

Samples of the product mixture were analyzed using a GC equipped with a FID detector. Thus, aromatic conversion was determined after the reaction, expressed as a percentage ratio of the converted o-xylol to the total o-xylol content in the feed. The results of the hydrogenation process using the catalysts of Examples 1 to 4 respectively are shown in the following table:

| Catalyst | Aromatic conversion (in %) |
|---|---|
| Comparative Example 1 | 78 |
| Example 2 (According to the Invention) | 98 |
| Example 3 (According to the Invention) | 97 |
| Example 4 (According to the Invention) | 93 |

A comparison of the results of the hydrogenation clearly shows the advantages of the catalysts and processes of the present invention. In particular, the conversion rate, i.e. the degradation of the aromatic compounds, is significantly higher using the process and catalyst of the present invention in comparison to the state of the art catalyst and process.

Comparison 2

The improved poison tolerance of preferred catalysts of the present invention is illustrated by a comparison of the hydrogenation runtimes of the catalysts of Examples 1, 5, 6 and 7 when using a feed comprising an enhanced concentration of sulphur.

The hydrogenation of a mixture of o-xylol and cyclohexane was carried out using catalysts according to Examples 1, 5, 6 and 7. The hydrogenation was carried out in an integral flow reactor (internal diameter of 25 mm). The integrated catalyst volume was 25 ml. Said 25 ml of catalysts were each introduced in 20 portions with 20 portions of SiC in a volume ratio of 1:3. Prior to catalytic reaction the catalysts were activated in a stream of hydrogen (50 l/h) at 250° C. over a period of 4 hours. As a feed a mixture of o-xylol and cyclohexane having a content of aromatics of 25 weight-% and a sulfur content of 100 ppm in the form of benzothiophene was employed. Further process conditions are the following: reaction pressure 30 bar, reaction temperature 180° C., LHSV 2 v/vh, ratio of gas/product 100 l H$_2$/l mixture of o-xylol-cyclohexane.

Aromatic conversion was determined, expressed as a percentage ratio of converted o-xylol to the total o-xylol content in the feed. The reaction time at which the aromatic conversion dropped to less than 99.9% was chosen as measure for the quality of the performance. The following results were observed:

| Catalyst | Runtime until aromatic conversion drops under 99.9% in h | Sulfur uptake in weight-% |
|---|---|---|
| Comparative Example 1 | 150 | 2.97 |
| Comparative Example 7 | 48 | 1.19 |
| Example 5 (According to the Invention) | 262 | 5.95 |
| Example 6 (According to the Invention) | 222 | 4.58 |

A comparison of the results of hydrogenation clearly shows the advantages of the catalysts according to the present invention. In particular, the runtime time is significantly higher using the process and catalyst of the present invention in comparison to the state of the art catalyst and process.

Comparison 3

For the evaluation of the sensitivity of the catalysts of the invention against chlorine components the following additional catalytic tests were carried out.

The reduced catalysts (each 1.5 g) are added under anaerobic conditions into a wire basket in an autoclave and treated with 200 ml of a cyclohexane-o-xylol-mixture with 25 weight-% of o-xylol and 200 ppm chlorine (source: heptylchloride) at a pressure of 40 bar, at a temperature of 130° C. and a stirring velocity of 2000 rpm (revolutions per minute) for 1 h. Samples of the product mixture were analyzed using a GC equipped with a FID detector.

Aromatic conversion was determined after 1 hour, expressed as a percentage ratio of converted o-xylol to the total o-xylol content in the feed. The following results were obtained:

| Catalyst | Aromatic conversion (in %) |
|---|---|
| Comparative Example 7 | 47.6 |
| Example 5 (According to the Invention) | 75.2 |
| Example 6 (According to the Invention) | 65.1 |

The results show that the catalysts according to the present invention are less sensitive to chlorine components in hydrogenation feeds and provide an improved conversion rate after one hour.

What is claimed is:

1. A nickel (Ni)-catalyst comprising a support and Ni, wherein the size distribution of the Ni crystallites is bimodal with 30 to 70% of the Ni crystallites having an average size (diameter) in the range of from 1.0 to 2.5 nm and the remaining Ni crystallites having an average size (diameter) in the range of from 3.0 to 4.5 nm, and wherein the Ni is distributed in an outer shell region of the catalyst and a remaining centre of the catalyst in a concentration ratio in the range of from 3.0:1 to 1.3:1, the outer shell region of the catalyst having a penetration depth of 3 to 15% of the catalyst diameter.

2. The Ni-catalyst according to claim 1 having a pore volume of 0.4 to 0.5 ml/g and wherein the portion of the pore volume having pore radii of >5.0 nm is at least 75%.

3. The Ni-catalyst according to claim 1, wherein the Ni content in the catalyst is 10 to 35 weight-%.

4. The Ni-catalyst according to claim 1, wherein the Ni content in the catalyst is 10 to 24 weight-% and the concentration ratio of Ni of the outer shell region to the Ni of the centre is 2.5:1 to 1.3:1.

5. The Ni-catalyst according to claim 1, wherein the Ni content in the catalyst is 24.1 to 35 weight-% and the concentration ratio of Ni of the outer shell region to the Ni of the centre is 3.0:1 to 1.5:1.

6. The Ni-catalyst according to claim 1, wherein the centre of the catalyst has a diameter in the range of from 300 to 500 μm.

7. The Ni-catalyst according to claim 1, wherein the specific Ni surface area is ≤135 m²/g Ni.

8. The Ni-catalyst according to claim 1, wherein the support comprises $Al_2O_3$, $Al_2O_3.SiO_2$ or a mixture thereof.

9. The Ni-catalyst according to claim 1, wherein the support is $Al_2O_3$ having a surface area in the range of from 100 to 220 m²/g or $Al_2O_3.SiO_2$ having a surface area in the range of from 120 to 200 m²/g.

10. The Ni-catalyst according to claim 8, wherein the support comprises $Al_2O_3.SiO_2$ and the $SiO_2$ content of the $Al_2O_3.SiO_2$ support is 2 to 8 weight-%.

11. The Ni-catalyst according to claim 1, wherein up to 30% of the total Ni in the catalyst by weight is in the outer shell region.

12. A Ni-catalyst comprising a support and nickel wherein a centre of the catalyst comprises a base Ni concentration and a remaining outer shell region of the catalyst comprises an increased Ni concentration, the centre having a diameter of at least 200 μm and the outer shell region having a penetration depth in the range of from 40 μm to 200 μm, wherein the size distribution of the Ni crystallites of the catalyst is bimodal, with 30 to 70% of the Ni crystallites having an average size (diameter) in the range of from 1.0 to 2.5 nm and the remaining Ni crystallites having an average size (diameter) in the range of from 3.0 to 4.5 nm.

13. A Ni catalyst comprising a support and nickel, wherein the size distribution of the Ni crystallites of the catalyst is bimodal, with 30 to 70% of the Ni crystallites having an average size (diameter) in the range of from 1.0 to 2.5 nm and the remaining Ni crystallites having an average size (diameter) in the range of from 3.0 to 4.5 nm, wherein a centre of the catalyst comprises a base Ni concentration and a remaining outer shell region of the catalyst comprises an increased Ni concentration.

14. The Ni-catalyst according to claim 1 further comprising at least 1 weight-% zinc (Zn) as a promoter.

\* \* \* \* \*